(12) United States Patent
Barat (10) Patent No.: US 10,067,606 B2
(45) Date of Patent: Sep. 4, 2018

(54) TOUCH SCREEN DISPLAY DEVICE AND METHOD OF TOUCH INPUT CONTROL

(71) Applicant: GENERAL ELECTRIC COMPANY, Schenectady, NY (US)

(72) Inventor: Venkatesh Barat, New Delhi (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 15 days.

(21) Appl. No.: 15/107,947

(22) PCT Filed: Sep. 15, 2014

(86) PCT No.: PCT/US2014/055588
§ 371 (c)(1),
(2) Date: Jun. 24, 2016

(87) PCT Pub. No.: WO2015/102685
PCT Pub. Date: Jul. 9, 2015

(65) Prior Publication Data
US 2016/0328084 A1    Nov. 10, 2016

(30) Foreign Application Priority Data
Dec. 31, 2013 (IN) .......................... 6197/CHE/2013

(51) Int. Cl.
*G06F 3/041* (2006.01)
*G06F 3/044* (2006.01)
(Continued)

(52) U.S. Cl.
CPC ............ *G06F 3/0418* (2013.01); *A61B 90/37* (2016.02); *A61M 16/01* (2013.01); *G06F 3/044* (2013.01);
(Continued)

(58) Field of Classification Search
CPC ...................................................... G06F 3/041
See application file for complete search history.

(56) References Cited

U.S. PATENT DOCUMENTS

2012/0038572 A1    2/2012  Kim et al.
2012/0146924 A1*   6/2012  Inoue .................... G06F 3/0418
                                                345/173
(Continued)

FOREIGN PATENT DOCUMENTS

EP    2154600 A2    2/2010
EP    2464099 A2    6/2012
(Continued)

OTHER PUBLICATIONS

International Search Report and Written Opinion for PCT/US2014/055588, dated Dec. 18, 2014, 11 pages.

*Primary Examiner* — Olga Merkoulova (57) ABSTRACT

A touchscreen display device and method of user input control therefor includes a graphical display that senses at least a touch down state and a touch off state at a plurality of locations displaying information. A processor is configured to receive the touch down states and touch off states at each of the plurality of locations. The processor is configured to measure an elapsed time from receipt of at least one touch down state at a subset of the plurality of locations. The processor further is configured to alter the display of information at the subset of locations if the touch down state persists beyond a predetermined elapsed time indicative of an interference.

20 Claims, 7 Drawing Sheets

(51) Int. Cl.
*G06F 3/0488* (2013.01)
*A61B 90/00* (2016.01)
*A61M 16/01* (2006.01)
*G06F 3/0481* (2013.01)
*G16H 40/63* (2018.01)
*A61B 5/00* (2006.01)
*A61M 16/00* (2006.01)

(52) U.S. Cl.
CPC ........ *G06F 3/0481* (2013.01); *G06F 3/04883* (2013.01); *G06F 3/04886* (2013.01); *G16H 40/63* (2018.01); *A61B 5/7475* (2013.01); *A61M 16/0051* (2013.01); *G06F 2203/04104* (2013.01)

(56) References Cited

U.S. PATENT DOCUMENTS

| | | | |
|---|---|---|---|
| 2012/0242617 A1 | 9/2012 | Lee | |
| 2012/0249470 A1* | 10/2012 | Sugiura | G06F 1/1694 345/174 |
| 2013/0009900 A1 | 1/2013 | Pryor | |
| 2013/0234987 A1* | 9/2013 | Ye | G06F 3/0418 345/174 |

FOREIGN PATENT DOCUMENTS

| | | | | |
|---|---|---|---|---|
| JP | 2011070250 | * | 7/2011 | ............ G06F 3/041 |
| WO | 0127867 A1 | | 4/2001 | |
| WO | 03052678 A1 | | 6/2003 | |

* cited by examiner

TOUCH SCREEN DISPLAY DEVICE AND METHOD OF TOUCH INPUT CONTROL

CROSS-REFERENCE TO RELATED APPLICATIONS

This application is a filing under 35 U.S.C. 371 of international application number PCT/US2014/055588, filed Sep. 15, 2014, which claims priority to Indian application number 6197/CHE/2013, filed Dec. 31, 2013, the entire disclosures of each are hereby incorporated by reference.

BACKGROUND

The present disclosure relates to the field of user input devices. More specifically, the present disclosure relates to a control of user input received at touch screen displays.

Touch screen displays are increasing in prevalence in many domains, including, but not limited to health care devices. Although touch screens are increasing in prevalence, touch screen suffer from susceptibility to inadvertent touches or contaminating on the touch screen which may limit operability or produced inadvertent inputs.

Introduction of touch screen into critical domains, exemplarily life support, anesthesia delivery, or other critical care medical settings further increases the risk of such susceptibilities.

BRIEF DISCLOSURE

An exemplary embodiment of a touch screen display device includes a graphical display that senses at least a touch down state and a touch off state at a plurality of locations displaying information. A processor is configured to receive the touch down states and touch off states at each of the plurality of locations. The processor starts a counter upon identifying a touch down state at a subset of the plurality of locations. The processor is further configured to alter the display of information of a subset of locations if the touch down state persists beyond a predetermined count associated with an interference.

An exemplary embodiment of a medical device configured to control a therapeutic interaction to a patient includes a graphical display. The graphical display operates to visually present information, operates to sense at least touch down states and touch off states. A graphical user interface (GUI) is presented on the graphical display. The GUI comprises a plurality of locations, a subset of the plurality of locations corresponds to a user input control.

A processor is communicatively connected to the graphical display. The processor operates the graphical display to present the GUI on the graphical display. The processor receives sensed touch down states and touch off states from the graphical display and operates to identify a location from the plurality of locations of the GUI associated with the touch down states and touch off states. The processor starts a counter if the processor identifies a location within the subset of the plurality of locations associated with a touch down state. If the touch down state persists beyond a predetermined count, the processor operates the graphical display to alter the GUI to visually present an alert.

An exemplary embodiment of a method of user input control includes presenting a graphical user interface (GUI) on a touch sensitive graphical display. The GUI includes a plurality of locations that include a first subset that presents at least one user input control and a second subset separate from the first subset. A processor receives at least one touch down state detected by the touch sensitive graphical display at a location within the plurality of locations of the GUI. An elapsed duration is counted since the received at least one touch down state. The elapsed duration since the received at least one touch down state is compared to a predetermined count threshold. If a touch release state is received at the processor before the elapsed duration exceeds the predetermined count threshold, the processor processes a touch input at a location within the plurality of locations of the GUI. If no touch release state is received at the processor before the elapsed duration exceeds the predetermined count threshold, the graphical user interface is operated by the processor to modify the GUI to visually present an alert.

DETAILED DISCLOSURE

Figure 1:
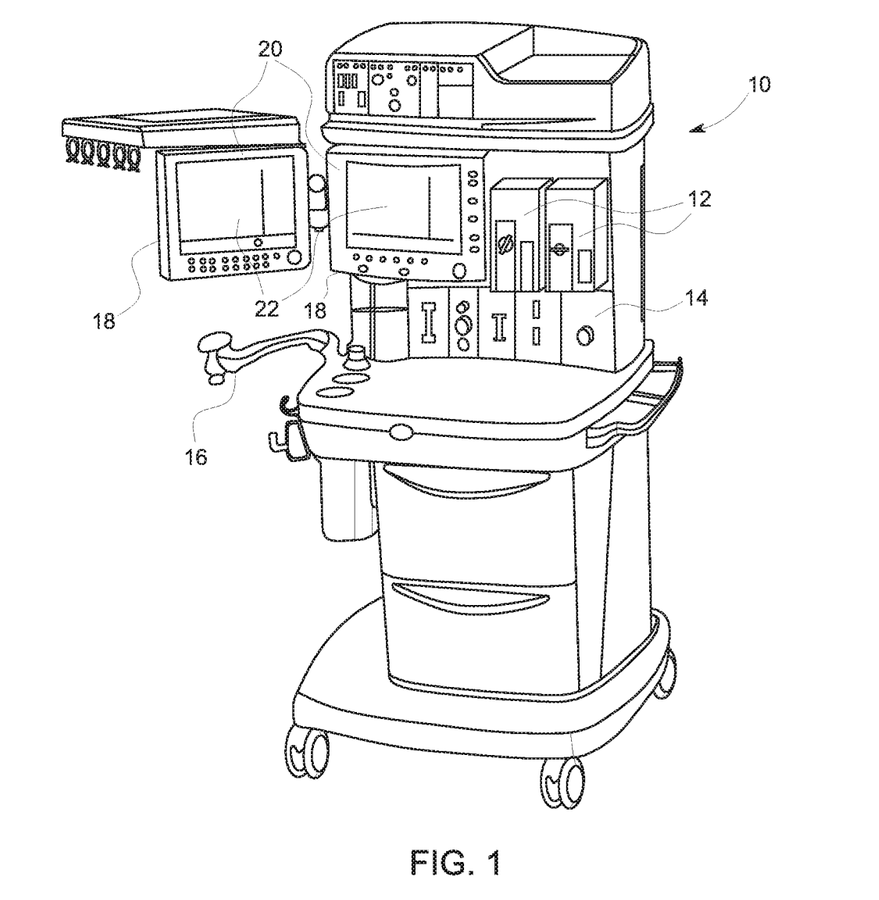
FIG. 1 depicts an exemplary embodiment of a medical device with a touch screen display.

FIG. 1 depicts an exemplary embodiment of a medical apparatus 10 which may be used in accordance with embodiments as disclosed herein. In a merely exemplary embodiment depicted in FIG. 1, the medical apparatus 10 is an anesthesia delivery apparatus; however, it will be recognized that embodiments as disclosed herein it may be used in connection with other types of medical apparatus, including, but not limited to a patient monitoring device, a medical imaging system, an anesthesia machine, or a vaporizer. It will also be recognized that embodiments as disclosed herein may be used in any of a variety of devices that use a touch sensitive display, including devices outside of the field of medical technology.

In the merely exemplary embodiment of the medical apparatus 10 depicted in FIG. 1, an anesthesia delivery machine includes sumps 12 in which anesthetic agent, and exemplarily inhaled anesthetic agent is stored in a liquid form until the anesthetic agent can be transitioned into a gaseous state by a vaporizer 14 and delivered to the patient (not depicted) through a patient connection 16.

In the exemplary embodiment as depicted herein, the medical apparatus 10 includes one or more touch screen display devices 18. In exemplary embodiments, the touch screen display device 18 includes a graphical display 20 that is operable to visually present a graphical user interface 22 that relays patient information and user input controls as will be described in further detail herein.

The graphical display 20, as noted above, is operable to receive single touch or multi-touch user inputs to the graphical display 20. In embodiments, this touch sensitive graphical display can detect touch interactions in a variety of manners, including, but not limited to, surface acoustic waves (SAW), capacitive, resistive, pressure, or other known touch interaction detection systems. The further exemplary embodiments as disclosed herein will exemplarily use a capacitive touch sensitive graphical display; however, this is merely for the sake of conciseness and is not intended to be limiting on the touch input detection systems as may be used with embodiments as disclosed herein.

Figure 2:
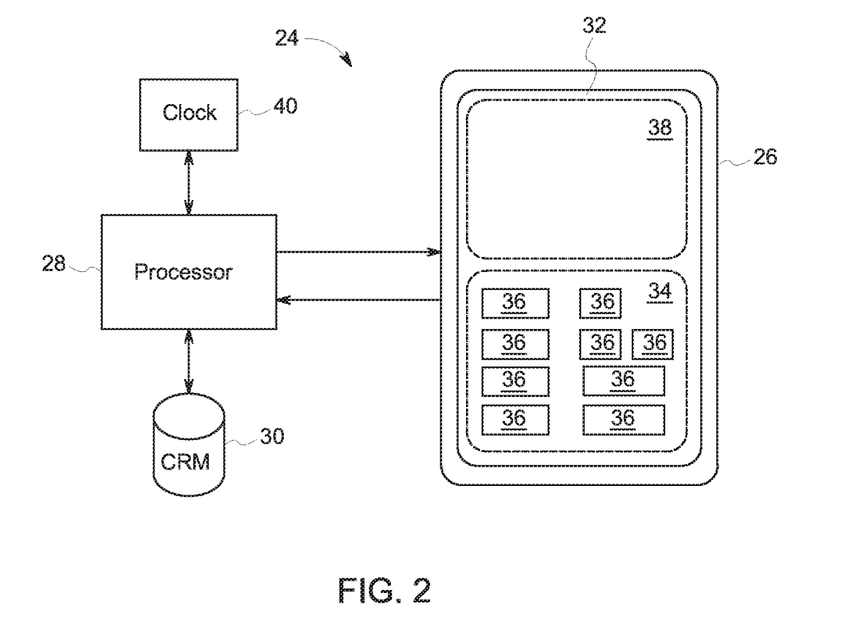
FIG. 2 depicts a schematic diagram of an exemplary embodiment of a touch screen display device.

FIG. 2 depicts a schematic diagram of an exemplary embodiment of a touch screen display device 24 as disclosed in further detail herein. The touch screen display device 24 includes a touch sensitive graphical display 26 that is operated by a processor 28. In an embodiment, the processor 28 is communicatively connected to a computer readable medium 30 upon which computer readable code is stored. The execution of the computer readable code causes the processor to carry out the functions and operations as disclosed herein. In an embodiment, the computer readable medium 30 may be one or more computer readable media communicatively connected to the processor, while in some embodiments, the computer readable media programmed with computer readable code may be an integral part of the processor 28.

The processor 28 operates the touch sensitive graphical display 26 such as to present a graphical user interface (GUI) 32 on the touch sensitive graphical display 26. As will be disclosed in further detail herein, the GUI 32 includes a plurality of locations generally divided into at least a first subset 34 which includes user input controls, exemplarily depicted in FIG. 2 as a plurality of button objects 36. The second subset of locations 38 is exemplarily three of user input controls, and may exemplarily be used to present information or graphical images to a user.

In operation, the processor 28 operates the touch sensitive graphical display 26 to visually present the GUI 32 while the touch sensitive graphical display 26 operates to detect user single or multi-touch inputs at specific locations at the touch sensitive graphical display 26. The processor 28 receives these detected touch inputs and associates the touch inputs to one or more of the user input controls of the GUI, such as the button object 36 of the first subset 34, and processes this user input.

Figure 3:
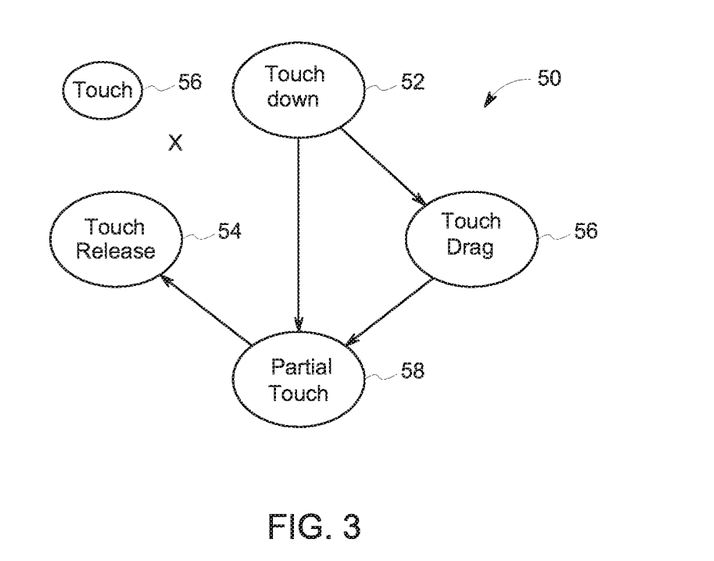
FIG. 3 is an exemplary state transition diagram in accordance with an embodiment of a touch screen device.

Referring now to FIGS. 2 and 3, FIG. 3 exemplarily depicts an embodiment of a state transition diagram 50 that depicts touch states that may be detected by the touch sensitive graphical display 26 and interpreted by the processor 28 as disclosed in further detail herein. An exemplary embodiment of any touch input begins with a touch down 52. In the non-limiting embodiment of a capacitance based touch sensitive graphical display, an interaction with the display by a conductive material or object will change a localized capacitance sensed at the locations surrounding the interaction between the substance or object and the touch sensitive graphical display. In a non-limiting embodiment, such an interaction may decrease the localized capacitance. A nominal threshold may be pre-established such that a decrease in capacitance below such a threshold is registered by the touch sensitive graphical display 26 as a touch down state. Similarly, when the conductive substance or object is removed from contact with the touch sensitive graphical display 26 the localized detected capacitance may return to a standard value such as to indicate a touch off state 54. In general, a touch input requires at least a transition between a touch down state 52 and a touch release state 54. The transition from the touch down state 52 to the touch release state 54, necessarily includes an intermediate partial touch state 58 as will be described in further detail herein. In exemplary embodiments, the same or another capacitance threshold as used to detect the touch down state 52 may similarly be used to detect the touch release state 54 as the capacitance increase after removal of the conductive substance or object from contact with the touch sensitive display 26. In still other embodiments, the capacitance threshold used to detect a touch down state 52 and a touch release state 54 may be different values, such as to adjust the sensitivity of the state detections, such that a smaller decrease in capacitance is detected as a touch down state 52, while a smaller increase from a localized minimum may be detected as a touch off state 54.

Figure 4A:
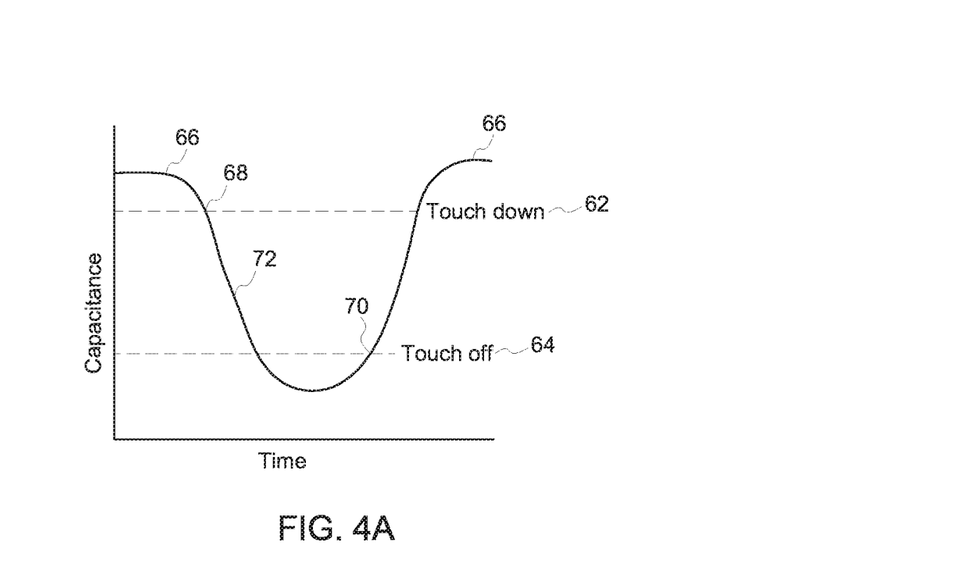
FIGS. 4A and 4B are graphs that depict exemplary embodiments of detected capacitance values.
Figure 4B:
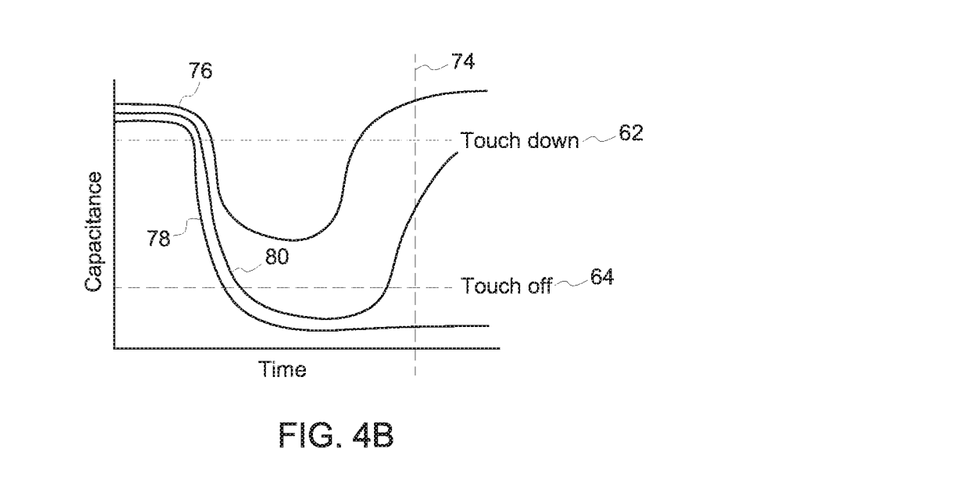

FIGS. 4A and 4B are graphs that exemplarily depict a localized capacitance value detected by the touch sensitive graphical display 26. It is to be understood that the graphs of FIGS. 4A and 4B are merely exemplary of relative statuses in accordance with FIG. 3. The graph depicts an exemplary embodiment wherein the predetermined touch down threshold 62 is a greater capacitance than the exemplary touch off threshold 64. The graph of FIG. 4A plots localized capacitance verses time and at reference 66 shows a neutral or normal state capacitance at the touch sensitive graphical display. At reference 68, the detected capacitance drops below the touch down threshold 62 and a touch down state 52 (FIG. 3) is detected. The capacitance continues to drop through the touch, and then upon release of the touch, the capacitance begins to return to the normal state capacitance value 66, crossing the touch off threshold 64 on the way back to the normal reference value 66 at touch off reference 70, indicating the touch off state 54 (FIG. 3).

Referring back to FIG. 3, between the touch down state 52 and the touch off state 54, an intermediate partial touch state 58 occurs. Referring to FIG. 4A, partial touch reference 72 indicates a range of capacitance values after the touch down state 52 has been initiated at touch down reference 68, but before the touch off has been detected at 70. In an exemplary embodiment, a partial touch state 58 (FIG. 3) is only detected if the capacitance achieves a value sufficient to result in the detection of a touch off state 54 (FIG. 3) at reference 70 (FIG. 4). Exemplarily, this occurs when the capacitance reaches the touch off threshold 64. In an alternative embodiment depicted in FIG. 3, if the partial touch state is combined with a change in the location of the detected capacitance shift, such a state may be indicated as a touch drag state 56 such as is representative of a more complex touch gesture exemplarily a drag gesture.

Referring back to FIG. 2, the touch screen display device 24 may further include a clock 40 communicatively connected to the processor 28; however, it will be recognized that in alternative embodiments, the clock 40 is an integral part of the processor 28. The processor 28 uses the clock 40 in order to initiate a measurement of an elapsed duration since a detected touch down state on the touch sensitive graphical display. As will be described in further detail herein, this measurement continues until either a touch event is detected or a predetermined elapsed duration threshold is exceeded. Referring now to FIG. 4B, three merely exemplary sensed capacitances are depicted, each exemplary of interactions that each exceed the predetermined elapsed duration threshold 74 before a touch event is detected, resulting in an identification of a touch screen interface. The graph of FIG. 4B exemplarily depicts the touch down threshold 62 and the touch off threshold 64 as described in further detail above. The graph of FIG. 4B further depicts an exemplary predetermined elapsed duration threshold 74 which marks a predetermined elapsed time duration from a first detection of a touch down state by a capacitance dropping below the touch down threshold 62. Capacitance 72 exemplarily depicts a detected capacitance wherein the touch down threshold 62 is crossed, but the capacitance never falls below the touch off threshold 64 and therefore a touch off state is never detected even as the capacitance returns to a normal capacitance level. Capacitance 78 depicts an exemplary embodiment wherein the touch off threshold 64 is crossed by the detected capacitance but the capacitance never increases to cross the touch off threshold 64 on an increasing trajectory in order to exemplarily indicate a touch off state 54, before the predetermined count duration 74 is crossed. In example capacitance 80, the touch off threshold 64 is crossed as the capacitance increases back towards the normal capacitance, but an exemplarily additional capacitance threshold, such as the touch down threshold 62, is not further crossed before the predetermined count duration 74 is reached. Each of these exemplary graphs may be interpreted as disclosed herein has an indication that an associated location on the touch sensitive graphical display is experiencing an interference and actions as disclosed herein are taken.

In still further embodiments, and as described herein in greater detail, the methods and systems may also detect and count a number of touch downs states detected at various locations on the touch sensitive display between the first touch down state and either the detection of a touch event or elapsed time reaching the predetermined elapsed duration threshold. This touch down count resets upon the detection of a touch event or exceeding the predetermined elapsed duration threshold. In exemplary embodiments, the touch down count is compared to a predetermined count threshold. If the touch down count exceeds this threshold, the systems or method as disclosed herein can further identify this as a touch screen interference.

Figure 5A:
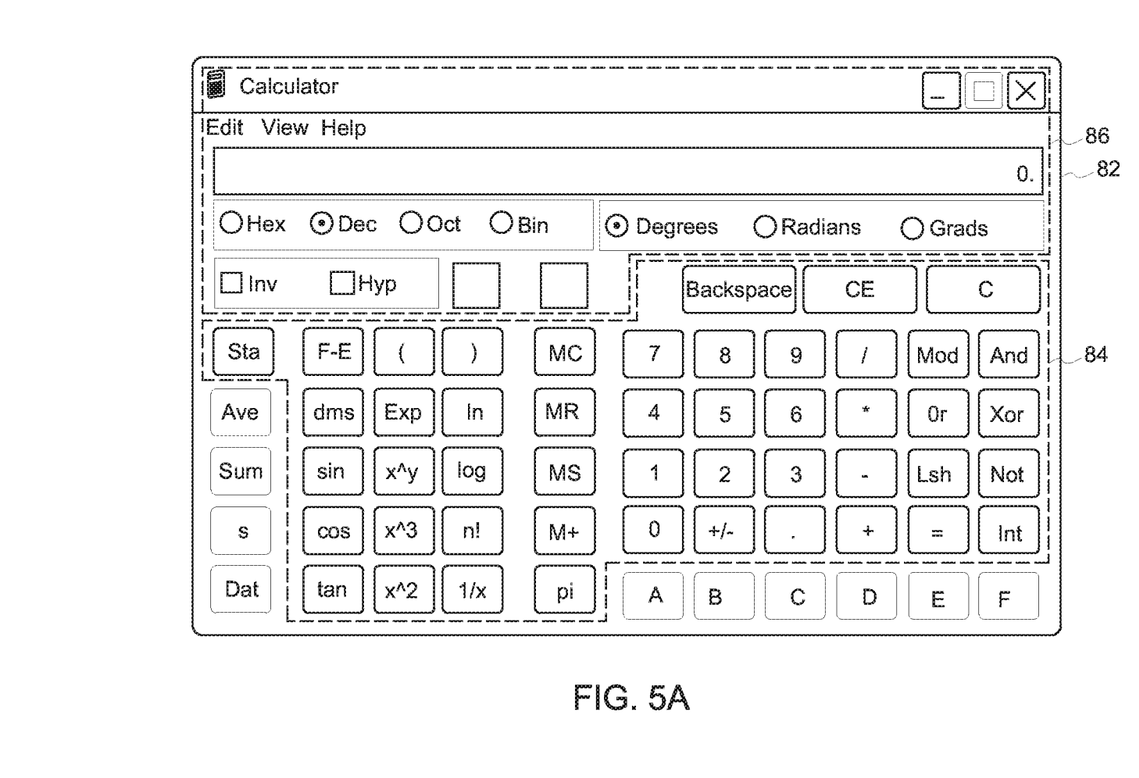
FIGS. 5A-5C depict exemplary embodiments of the GUI as disclosed herein.
Figure 5B:
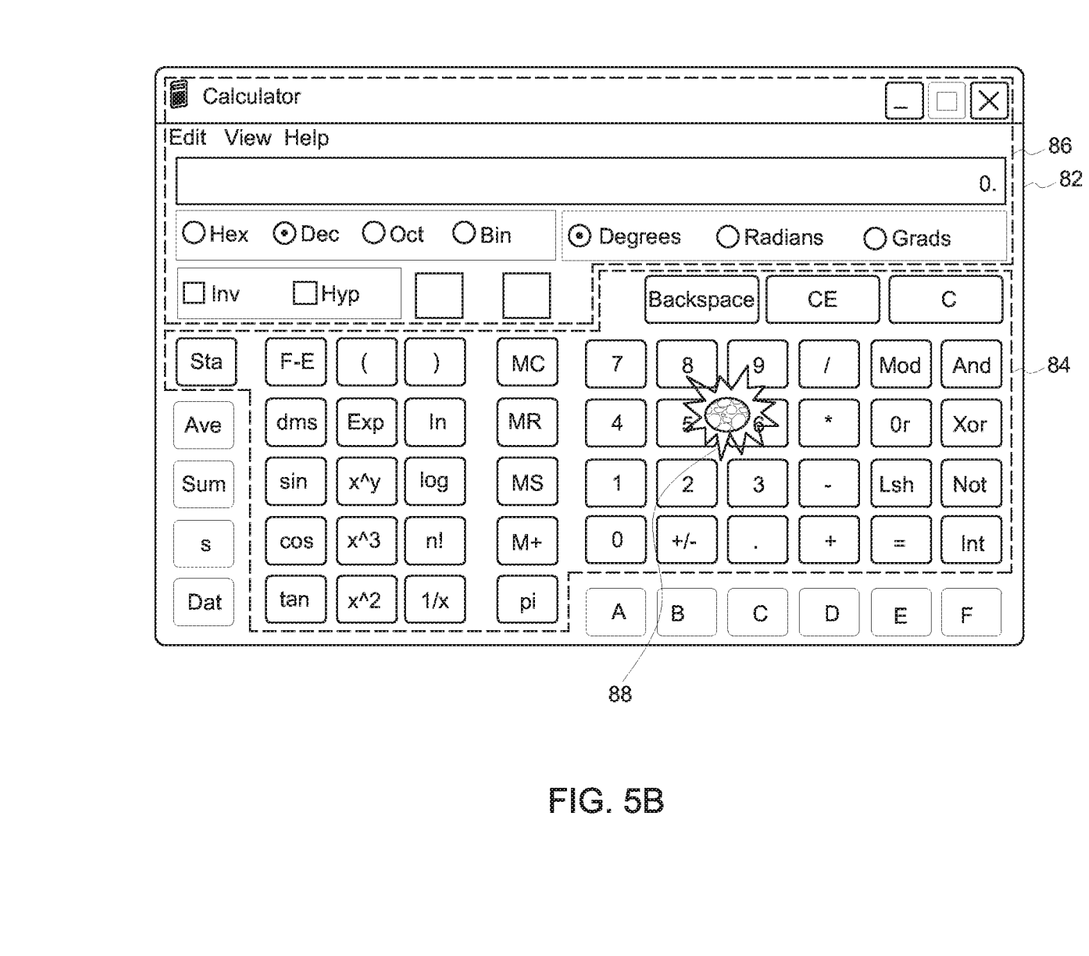
Figure 5C:
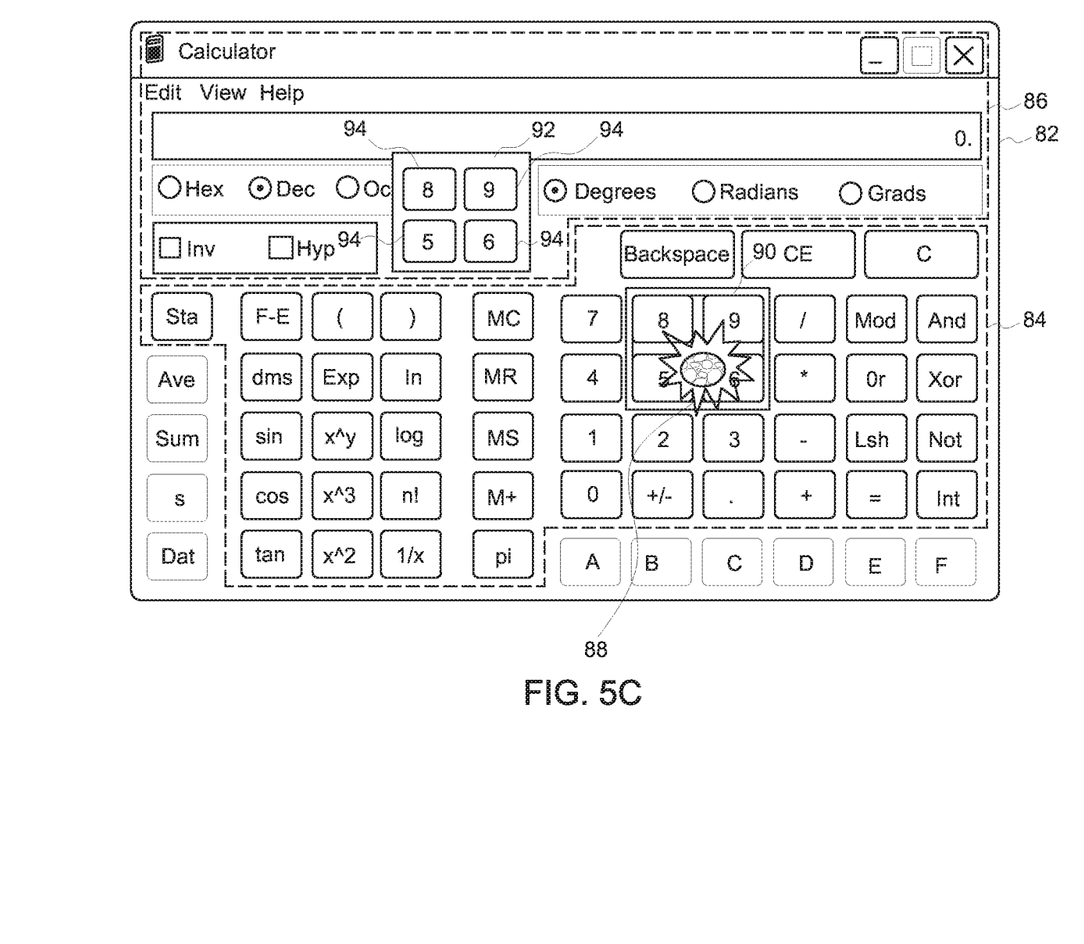

FIGS. 5A-5C graphically depict an embodiment of the operation of the graphical user interface as disclosed herein. FIG. 5A depicts a merely exemplary embodiment of a graphical user interface (GUI) 82. While the GUI 82 is exemplarily depicting a calculator GUI, it will be understood that this application is merely exemplary of a GUI that may be operated in accordance with the devices and method as disclosed herein. The GUI 82 further includes at least a first subset of location 84 that include use input controls, such as may be operated with touch inputs and a second subset of locations 86 that are either don't include user input controls or include low priority functionalities that may be deemed as of secondary importance to the user input controls found in the first subset 84.

In FIG. 5B an exemplary representation of a contaminating substance that lands on the touch sensitive graphical display in the first subset of locations 84. In the exemplary embodiment of a medical device, such contaminant may be a liquid such as, but not limited to water, saline, blood, or other bodily fluids. However, it is to be understood that such contaminating substances may alternatively be another substance such as food or tissue. In any event, the contaminating substance 88 results in a detected continuous touch down, a partial touch state or touch drag state, without a detected touch off state before the predetermined elapsed duration threshold. While in an embodiment wherein the touch sensitive graphical display is oriented at a sufficient angle to the vertical and the determining substance 88 is of a low enough viscosity then the contaminating substance 88 may move down the GUI 82 due to gravity and a touch drag state 56 may be detected. In any event since the interaction of the contaminating substance is not detected as an actual touch event, the predetermined count duration 74 from the detection of the touch down state will be exceeded and the processor will identify that the touch screen is experiencing an interference. In another embodiment, the contaminating substance may be an aerosol or a plurality of droplets. This may be detected as a plurality of town downs, which may on their own exceed a predetermined touch down count resulting in an interference detection before reaching the predetermined elapsed duration threshold.

At FIG. 5C, exemplary remedial actions to the detected interference are depicted. After the interference from the contaminating substance 88 is detected, a compromised area is calculated and the GUI 82 is modified to present one or more alerts of the interference. In an embodiment, the compromised area is computed as a minimal, but sufficient surface area that encloses the locus of all existing touch downs, partial touches, or touch drags. In a further embodiment, this may be a geometric shape, such as a square, rectangle, or polygon. The alerts may be visual, textual indication that the touch sensitive display is experiencing interference, while in other embodiments, the alert may be an audible alert produced by a sound generator or a visual alert produced by illuminating a light associated with the graphical display. In the embodiment depicted in FIG. 5C, a highlighted boundary 90 is placed around the calculated compromised area to indicate to a user, the area that has been calculated to be compromised. This may be accompanied by a disabling of the receipt to touch inputs from within the compromised area. In FIG. 5C, the GUI 82 is further modified such as to relocate the compromised area to a location within the second subset of locations 86. The relocated user input controls 92 thus reproduced the functionality of the compromised area which in the example depicts includes the presentation of a plurality of button objects 94.

It will be understood that in embodiments, the GUI 82 may be further modified to present an input control (not depicted) to dismiss the relocated input control, and the interference alerts as presented herein. In an alternative embodiment, such a dismissal may be entered by a single or multi-touch input into the touch sensitive graphical display by the user.

Figure 6:
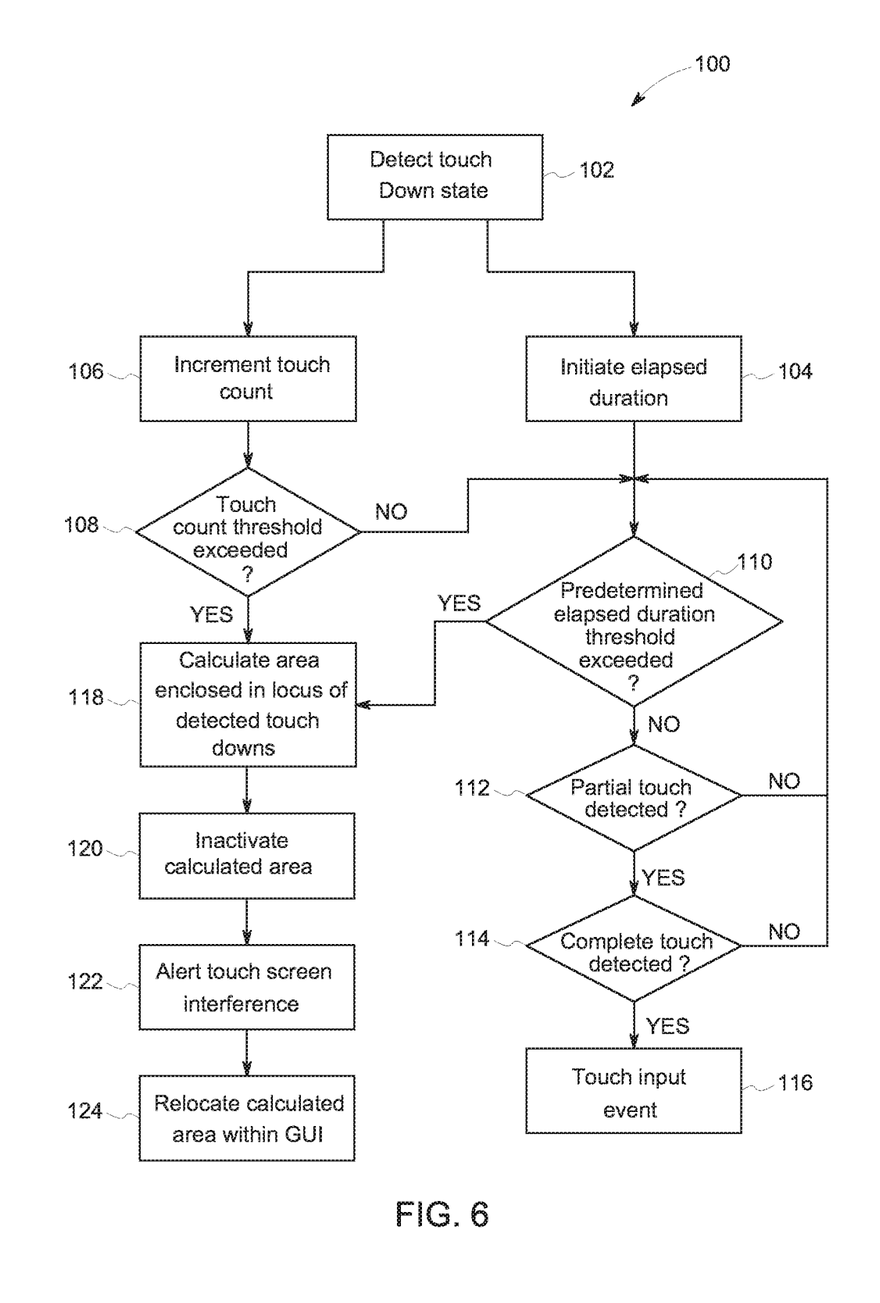
FIG. 6 is a flow chart that depicts and exemplary embodiment of a method of user input control.

FIG. 6 is a flow chart of an exemplary embodiment of a method 100 of user input control. It is to be understood that in an exemplary embodiment, a graphical user interface (GUI) is presented on a touch sensitive graphical display. The GUI includes a plurality of locations in a first subset of locations that present at least one user input control and a second subset of locations separate from the first subset. At 102 at least one touch down state is detected by a processor. At 104 a timer is initiated which measures an elapsed duration since the detected at least one touch down state. At 106 a touch count is incremented with the newly detected touch down state from 102. The incremented touch count within a short duration can be indicative of a number of individual locations at which the touch downs from a subset of the GUI objects portion of the user interface of the touch sensitive display which is compromised. At 108 the incremented touch count from 106 is compared to a touch count threshold, which represents a predetermined threshold number of touch downs that may be received within the predetermined elapsed duration as described herein associated with a single interaction with the touch sensitive display. As will be described in further detail herein, if the touch count threshold is exceeded at 108, then remedial actions may be taken to address the interference with the touch sensitive display.

If the touch count threshold has not been exceeded (e.g. after a first detected touch down state), then the elapsed duration since the detected touch down state from 104 is compared to a predetermined elapsed duration threshold at 110. As described above, if the predetermined elapsed duration threshold is exceeded, then an interference with the touch sensitive display is detected and remedial actions as disclosed herein are taken. If the predetermined elapsed duration is not exceeded, then the sensed touch is processed in an effort to detect a touch input event. First, it is determined if a partial touch state has been detected at 112. If no partial touch state is detected, then the method returns to step 110 to compare the elapsed duration to the predetermined elapsed duration threshold. If a partial touch state is detected at 112, then the touch signal is further analyzed to determine if a complete touch has occurred at 114. In such embodiment, the complete touch is detected upon the occurrence of the touch off state. If a complete touch has occurred at 114, then this is interpreted as a touch input event at 116 and an input or action in accordance with the touch input event detected at 116 is entered or initiated. Therefore, in the embodiment, a touch input event is detected after detection of a touch down, partial touch, and touch off states. If no complete touch is detected at 114, then the elapsed duration sensed the touched down state is again compared to the predetermined elapsed duration threshold at 110. If at any point, predetermined elapsed duration threshold is exceeded at 110, then an interference with the touch sensitive display is detected.

As stated above, if the predetermined elapsed duration threshold is exceeded at 110, then remedial action may be taken as the touch sensitive display is determined to be compromised. At 118, an area enclosed in the locus of all of the detected touch down states (e.g. those counted at 106) is calculated. This compromised area may be calculated by creating a minimum boundary that surrounds all of the detected touch down states which may have been incremented in the touch count at 106. In a further embodiment, the calculated area may further take into account the graphical user interface and associated user input controls presented in the locus of the detected touch down states such that the calculated area creates a minimized area that includes the entirety of any user input controls containing located touch downs.

At 120 the calculated compromised area of the graphical user interface is inactivated from receiving any further touch input events and at 122 a touch screen interference is alerted. As described above, the touch screen interference alerts may include any of a variety of audio and/or visual alerts. While in still further embodiments, the alerts may be made exemplarily at remote or centralized locations, such that personnel apart from the touch sensitive display are made aware of the interference. In a still further embodiment, the graphical user interface and touch sensitive display enter a safe state, disabling all entry of touch input events until the detected interference is either remediated or dismissed. Finally, at 124 the calculated compromised area is relocated with in the GUI. As described above, in an exemplary embodiment, the calculated compromised area is relocated to a location within a subset of locations within the GUI that do not include user input controls, such as to maximize continued functionality, of the GUI without losing any functionality to provide the relocated calculated compromised area. As previously indicated, the graphical user interface may also present a user input control such as to dismiss the interference and the remedial actions taken because of the detected interference, or alternatively the remedial action may be dismissed with another single or multi-touch user input gesture.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A touchscreen display device, comprising:
   a graphical display that senses at least touch down states and touch off states at a plurality of locations displaying information; and
   a processor configured to:
      receive the touch down states and touch off states at each of the plurality of locations;
      count newly detected touch down states within a predetermined elapsed time;
      if a count of the newly detected touch down states exceeds a predetermined threshold number, calculate an area in locus of the newly detected touch down states and alter the display of the information in the area;
      measure an elapsed time from receiving at least one touch down state at a subset of the plurality of locations; and
      alter the display of information at the subset of locations if the touch down state persists beyond the predetermined elapsed time indicative of an interference.

2. The touchscreen display device of claim 1, wherein the subset of locations corresponds to a user input control and the processor is configured to relocate the user input control to a non-overlapping subset of locations if the touch down state persists beyond the predetermined elapsed time indicative of an interference.

3. The touchscreen display device of claim 1, wherein the touchscreen display device is part of a medical device.

4. The touchscreen display device of claim 3, wherein the medical device is selected from a patient monitor, medical imaging system, an anesthesia machine, and a vaporizer.

5. The touchscreen display device of claim 1, wherein the graphical display is a multi-touch display device.

6. The touchscreen display device of claim 1, further comprising:
   a graphical user interface (GUI) presented on the graphical display by the processor, the graphical user interface comprising at least one user input control at the subset of the plurality of locations.

7. The touchscreen display device of claim 6, wherein if the touch down state persists beyond the predetermined elapsed time, the processor operates the graphical display to modify the GUI to present a visual alert associated with the subset of the plurality of locations.

8. The touchscreen display device of claim 7, wherein if the touch down state persists beyond the predetermined elapsed time, the processor further operates to disable user inputs received by the graphical display within the subset of the plurality of locations.

9. The touchscreen display device of claim 8, wherein the subset of the plurality of locations is a first subset of the plurality of locations and if the touch down state persists beyond the predetermined elapsed time, the processor further operates the graphical display to modify the GUI to relocate the user input control within the GUI to a second subset of the plurality of locations that is separate from the first subset of the plurality of locations.

10. The touch screen display device of claim 9, wherein the processor receives a plurality of touch down states and wherein the subset of the plurality of locations is a compromised area of the GUI identified by the processor from locations of the received plurality of touch down states.

11. The touchscreen display device of claim 1, wherein the area in locus of the newly detected touch down states is a minimum boundary that surrounds all of the newly detected touch down states.

12. A medical device configured to control a therapeutic interaction to a patient, the medical device comprising:
 a graphical display that operates to visually present information and operates to sense at least touch down states and touch off states;
 a graphical user interface (GUI) presented on the graphical display that comprises a plurality of locations, a subset of the plurality of locations corresponding to a user input control; and
 a processor communicatively connected to the graphical display, the processor operates the graphical display to present the GUI on the graphical display, the processor is configured to:
  receive sensed touch down states and touch off states from the graphical display;
  identify locations from the plurality of locations of the GUI associated with the touch down states and touch off states;
  count newly sensed touch down states within a predetermined elapsed duration threshold;
  if a count of the newly sensed touch down states exceeds a predetermined threshold number, calculate an area in locus of the newly detected touch down states and operate the graphical display to alter the GUI in the area;
  measure an elapsed duration from when the processor identifies a location within the subset of the plurality of locations associated with a touch down state, and
  if a touch off state is not received before the predetermined elapsed duration threshold, operate the graphical display to alter the GUI to visually present an alert.

13. The medical device of claim 12, wherein the processor further identifies if the identified first location is within the subset of the plurality of locations corresponding to the user input control, and calculates a comprised area with the subset.

14. The medical device of claim 13, wherein the processor operates to the disable the calculated compromised area from receiving user inputs.

15. The medical device of claim 14, wherein the visually presented alert visually identifies the calculated compromised area within the subset of the plurality of locations associated with the touch down state.

16. The medical device of claim 15, wherein the processor operates the graphical display to alter the GUI to visually present at least one user input control of the calculated compromised area in a location of the GUI outside of the subset of the plurality of locations corresponding to the user input control subset of the plurality of locations.

17. A method of user input control, the method comprising:
 presenting a graphical user interface (GUI) on a touch sensitive graphical display, the GUI comprising a plurality of locations comprising a first subset of locations that presents at least one user input control and a second subset of locations separate from the first subset;
 receiving at a processor touch down states and touch release states detected by the touch sensitive graphical display at the plurality of locations of the GUI;
 counting newly detected touch down states within a predetermined elapsed duration threshold;
 if a count of the newly detected touch down states exceeds a predetermined threshold number, calculating an area in locus of the newly detected touch down states and altering the GUI in the area;
 counting an elapsed duration from receiving at least one touch down state; and
 comparing the elapsed duration to the predetermined elapsed duration threshold;
 wherein if a touch release state is received at the processor before the elapsed duration exceeds the predetermined count threshold, processing, with the processor, a touch input at the location within the plurality of locations of the GUI; and
 wherein if no touch release state is received at the processor before the elapsed duration exceeds the predetermined count threshold, operating the graphical display with the processor to modify the GUI to visually present an alert.

18. The method of claim 17, further comprising:
 identifying with the processor if the touch down state is detected by the touch sensitive graphical display at a location within the first subset; and
 calculating a comprised area within the first subset.

19. The method of claim 18, further comprising:
 operating the graphical display to modify the GUI to visually present an indication of the calculated compromised area; and
 operating the graphical display to modify the GUI to relocate at least one user input from the first subset compromised area from the first subset to the second subset of locations.

20. The method of claim 18, further comprising:
 calculating a compromised area within the first subset from locations of the received at least one touch down state.

* * * * *